US00PP16118P3

(12) United States Plant Patent
Hofmann

(10) Patent No.: US PP16,118 P3
(45) Date of Patent: Nov. 15, 2005

(54) **NEW GUINEA *IMPATIENS* PLANT NAMED 'FISUPNIC LIPINK'**

(50) Latin Name: *Impatiens hawkeri*
Varietal Denomination: Fisupnic Lipink

(75) Inventor: Birgit C. Hofmann, Bendorf (DE)

(73) Assignee: Florfis AG, Binningen (SE)

( * ) Notice: Subject to any disclaimer, the term of this patent is extended or adjusted under 35 U.S.C. 154(b) by 56 days.

(21) Appl. No.: 10/829,217

(22) Filed: Apr. 22, 2004

(65) Prior Publication Data

US 2004/0216202 P1 Oct. 28, 2004

(30) Foreign Application Priority Data

Apr. 22, 2003 (CH) ..... 03-1996

(51) Int. Cl.[7] ..... A01H 5/00
(52) U.S. Cl. ..... Plt./318
(58) Field of Search ..... Plt./318

(56) References Cited

U.S. PATENT DOCUMENTS

PP10,109 P * 11/1997 Trees ..... Plt./318
PP11,706 P * 12/2000 Klemm ..... Plt./318
PP13,180 P2 * 11/2002 Strope ..... Plt./138
PP13,579 P2 * 2/2003 Hofmann ..... Plt./138
PP13,714 P2 * 4/2003 Hofmann ..... Plt./318
2002/0174469 P1 * 11/2002 Strope ..... Plt./318
2004/0216202 P1 * 10/2004 Hofmann ..... Plt./318

OTHER PUBLICATIONS

UPOV ROM GTITM Computer Database, GTI Jouve Retrieval Software 2004/06 Citatation(s) for 'Fisupnic Lipink'.*

* cited by examiner

*Primary Examiner*—Howard J. Locker
*Assistant Examiner*—W. C. Haas
(74) *Attorney, Agent, or Firm*—Foley & Lardner, LLP

(57) ABSTRACT

A new and distinct cultivar of New Guinea *Impatiens* plant named 'Fisupnic Lipink', and particularly characterized by the combined features of light pink to nearly white flowers with purple eyes; large, round, flat flowers; uniform, deep green foliage; moderately tall, rounded plant habit; and early to medium flowering response.

1 Drawing Sheet

Botanical description: *Impatiens hawkeri.*
Variety denomination: 'Fisupnic Lipink'.

BACKGROUND OF THE INVENTION

The present invention comprises a new and distinct cultivar of New Guinea *Impatiens* plant, botanically known as *Impatiens hawkeri*, and hereinafter referred to by the cultivar name 'Fisupnic Lipink'.

'Fisupnic Lipink' is a product of a planned breeding program and originated from a hybridization made by the inventor, Birgit C. Hofmann, in a controlled breeding program in Hillscheid, Germany, in 2000.

The female parent was the variety 'Malita' (unpatented), characterized by carmine and orange mixed flower color, flowers with a purple center, medium to light green foliage, and fairly compact plant habit.

The male parent of 'Fisupnic Lipink' was 'Fisimp 131' (U.S. Plant Pat. No. 13,714), characterized by round, rose-red flowers, medium green foliage, medium sized, and round and tight plant habit.

'Fisupnic Lipink' was discovered and selected as one flowering plant within the progeny of the stated cross by the inventor in April, 2001 in a greenhouse in Galdar, Gran Canaria, Spain.

The first act of asexual reproduction of 'Fisupnic Lipink' was accomplished when vegetative cuttings were taken from the initial selection in July, 2001 in a controlled environment in Galdar, Gran Canaria, Spain, by, or under the supervision of the inventor.

Horticultural examination of plants grown from these cuttings initiated in the spring of 2002 in Hillscheid, Germany, and continuing thereafter, has demonstrated that the combination of characteristics as herein disclosed for 'Fisupnic Lipink' are firmly fixed and are retained through successive generations of asexual reproduction. The new cultivar reproduces true to type.

'Fisupnic Lipink' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under greenhouse conditions which approximate those generally used in commercial practice.

BRIEF SUMMARY OF THE INVENTION

The following traits have been repeatedly observed and are determined to be basic characteristics of 'Fisupnic Lipink', which in combination distinguish this *Impatiens* as a new and distinct cultivar:

1. light pink to nearly white flowers with purple eyes;
2. large, round, flat flowers;

3. uniform, deep green foliage;
4. moderately tall, rounded plant habit; and
5. early to medium flowering response.

Of the many commercial cultivars known to the inventor, the most similar in comparison to 'Fisupnic Lipink' is the patented variety 'Fisnics Light Pink' (U.S. Plant Pat. No. 13,579).

In comparison to 'Fisnics Light Pink', 'Fisupnic Lipink' has a more variable pink flower color, and much taller, more upright plant habit.

BRIEF DESCRIPTION OF THE DRAWING

The accompanying photographic drawing shows typical flower and foliage characteristics of 'Fisupnic Lipink' with colors being as true as possible with illustrations of this type.

The photographic drawing shows a side view of a typical flowering plant of 'Fisupnic Lipink'.

DETAILED BOTANICAL DESCRIPTION

In the following description color references are made to The Royal Horticultural Society Colour Chart (R.H.S.). The color values were determined indoors from plants growing in a green-house in May 2003, Hillscheid, Germany.

The description is based on plants which were planted as rooted cuttings in 12 cm pots in late February 2003, and then grown in the greenhouse at a minimum temperature of 16° C. Most observations and measurements were made after the beginning of flowering in mid May, when the plants were about 12 weeks old.

PLANT

General appearance and form:

*Plant habit.*—Tall and upright, surface of foliage canopy rounded, and well-branched; growth is indeterminate, though weak after beginning of flowering.

*Height.*—17.9 cm.

*Width.*—31.3 cm.

*Number of branches.*—Approximately 11.5 per plant.

*Length of branches.*—12 to 14 cm.

*Internode length.*—5.5 to 7.0 cm.

*Diameter of branches.*—8 to 9 mm.

*Stem color.*—Brown, RHS 178 C.

*Propagation.*—Terminal shoot tips for cuttings.

*Rooting.*—Roots initiate in about 18 days at 22° C., from sticking to transplanting.

*Cultivation time.*—It takes about 9 to 10 weeks of growing time to produce a marketable flowering plant in a 12 cm pot.

Foliage:

*Leaf arrangement.*—Primarily in whorls.

*Shape of leaf.*—Elliptic, with acute base and acuminate tip.

*Texture.*—Surface slightly glossy, smooth or faintly rippled.

*Margin.*—Slightly serrated, ciliated.

*Leaf length.*—13.3 cm.

*Leaf width.*—4.2 cm.

*Upper surface, main color.*—Medium to dark green, uniform; mature leaves between RHS 137 A and 139 A, young leaves near RHS 137 A.

*Veins on upper surface color.*—Dark red, RHS 183 C, near the base.

*Lower surface color.*—Light green, about RHS 139 C (both young and mature leaves).

*Veins on lower surface color.*—RHS 183 A.

*Petiole.*—2.2 cm in length, 3 mm in diameter.

*Petiole color.*—Upper side dark-red, RHS 185 A, lower side RHS 185 A.

INFLORESCENCE

*Flowering response.*—9 weeks after planting of rooted cuttings.

*Flowering season.*—Generally indeterminate, mainly from March to October, depending on light intensity.

Flower:

*Number of flowers per node.*—6 to 8, in various stages of development.

*Form of corolla.*—Single-type, 5 petals.

*Shape of corolla.*—Large, nearly round, with the petals overlapping, almost flat.

*Diameter of corolla.*—Average length: 75 mm. Average width: 75 mm. Depth of corolla: 10 mm.

*Shape of petals.*—Cordate, only weakly lobed at the top end, base attenuate. Top petal: 32 mm long, 52 mm wide. Lateral petals: 35 mm long, 40 mm wide. Lower petals 37 mm long, 48 mm wide. Texture: Smooth ,velvety. Aspect: Flat.

*Color (general tonality from a distance of three meters).*—Light pink to nearly white, somewhat variable ground color, with a small purple eye.

*Color of upper surface.*—Light pink RHS 65 A to RHS 69 D, nearly white.

*Color of eye zone.*—Red-purple, RHS N 66 B.

*Color of lower surface.*—Mainly pale light pink, RHS 69 C.

*Spur.*—Downwardly curved, 6.7 mm long, 3 mm in diameter at the flower end; color deep pink, RHS 63 B.

*Peduncle color.*—Pink, RHS 63 C.

*Peduncle length.*—Approximately 50 mm.

*Flower bud.*—Ovoid shape, 24 mm in length, 16 mm in width; color RHS 69 B.

Reproductive organs:

*Stamens.*—5 in number, fused, upper surface color is RHS N57 C.

*Anthers.*—Fused, hooded.

*Pollen.*—Whitish-yellow, about RHS 8 D.

*Style and stigma.*—Five in number, very short, yellowish, about RHS 150 D.

*Ovary.*—5-celled, 5 mm long, surface green, RHS 139 B.

Disease/pest resistance/susceptibility: No observations to date.

I claim:

1. A new and distinct New Guinea *Impatiens* Plant named 'Fisupnic Lipink' as described and illustrated herein.

* * * * *

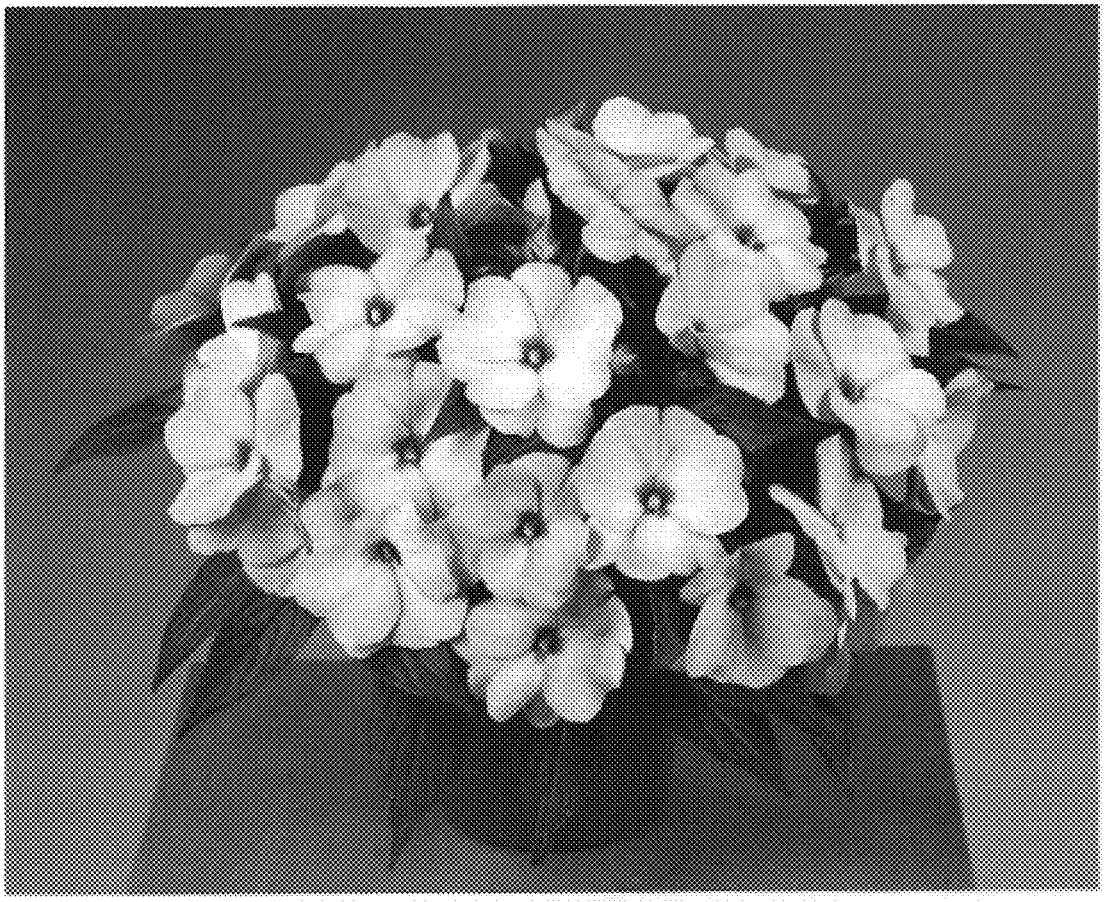

UNITED STATES PATENT AND TRADEMARK OFFICE

CERTIFICATE OF CORRECTION

PATENT NO. : PP 16,118 P3
DATED : November 15, 2005
INVENTOR(S) : Birgit C. Hofmann It is certified that error appears in the above-identified patent and that said Letters Patent is hereby corrected as shown below:

Title page,
Item [73], Assignee, should read:
-- Florfis AG, Binningen (CH) --.

Signed and Sealed this

Eleventh Day of April, 2006

JON W. DUDAS
*Director of the United States Patent and Trademark Office*